United States Patent
Dilber et al.

(10) Patent No.: US 9,585,914 B2
(45) Date of Patent: Mar. 7, 2017

(54) EXPANDED NK CELLS

(71) Applicant: Cellprotect Nordic Pharmaceuticals AB, Stockholm (SE)

(72) Inventors: Sirac Dilber, Huddinge (SE); Evren Alici, Gnesta (SE)

(73) Assignee: CELLPROTECT NORDIC PHARMACEUTICALS AB, Stockholm (SE)

( * ) Notice: Subject to any disclaimer, the term of this patent is extended or adjusted under 35 U.S.C. 154(b) by 0 days.

(21) Appl. No.: 14/830,758

(22) Filed: Aug. 20, 2015

(65) Prior Publication Data
US 2015/0374754 A1 Dec. 31, 2015

Related U.S. Application Data

(63) Continuation of application No. 11/938,123, filed on Nov. 9, 2007.

(51) Int. Cl.
  *A61K 35/17* (2015.01)
  *A61K 35/12* (2015.01)
  *C12N 5/0783* (2010.01)
  *A61K 39/00* (2006.01)

(52) U.S. Cl.
  CPC ............ *A61K 35/17* (2013.01); *C12N 5/0646* (2013.01); *A61K 35/12* (2013.01); *A61K 2035/124* (2013.01); *A61K 2039/5158* (2013.01); *C12N 2500/90* (2013.01); *C12N 2501/23* (2013.01); *C12N 2501/515* (2013.01)

(58) Field of Classification Search
None
See application file for complete search history.

(56) References Cited

U.S. PATENT DOCUMENTS

2003/0068306 A1  4/2003  Dilber

FOREIGN PATENT DOCUMENTS

WO  WO2006052534  5/2006

OTHER PUBLICATIONS

Ljunggren and Malmberg (Nature Rev., 5/07, 7: 329-339).*
Suck et al (Hematol. Oncol. Stem Cel. Ther. 2010, 3(3): 135-142).*
Thomas S. 2008, Everyday Health, 1 page.*
Barlogie et al:"Multiple myeloma and chronic lymphocytic leukemia parallels and contrasts", The American Journal of Medicine, Oct. 1992, vol. 93, p. 443.
Alter et al:"CD107a as a functional marker for the identification of natural killer cell activity", Journal Immunological Methods, (2004), vol. 294, pp. 15-22.
Fauriat:"Impaired activating receptor expression pattern in natural killer cells from patients with multiple myeloma", Leukemia (2006) 20, 732-733. doi:10.1038/sj.leu.2404096. Published online Jan. 26, 2006.
McMaster et al:"Waldenström macroglobulinaemia and IgM monoclonal gammapathy of undetermined significance: emerging understanding of a potential precursor condition", British Journal of Haematology, 139, 663-671.
Carlens et al: "A New Method for In Vitro Expansion of Cytotoxic Human CD3-CD56+ Natural Killer Cells", Human Immunology (2001), 62, 1092-1098, Published by Elsevier Science Inc.
Vogt et al:"Overview of monoclonal gammopathies of undetermined significance", British Journal of Haematology, 2007,139, 687-689.
Landgren et al:"Multiple myeloma, chronic lymphocytic leukaemia and associated precursor diseases", British Journal of Haematology, 2007, 139, 717-723.
Alici et al:"Autologous antitumor activity by NK cells expanded from myeloma patients using GMP-compliant components", Blood, Mar. 15, 2008, vol. III, No. 6, 3155-3162.

* cited by examiner

*Primary Examiner* — Gerald R Ewoldt
*Assistant Examiner* — Marianne Dibrino
(74) *Attorney, Agent, or Firm* — Gabriela B. Tomescu; Bergenstråhle & Partners AB (57) ABSTRACT

The present invention relates to expanded NK cells. The NK cells have been expanded ex vivo, are activated and have a cytotoxic phenotype. The cytotoxicity against malignant cells is markedly increased compared to non-expanded NK cells. The invention also relates to a method of treatment.

6 Claims, 8 Drawing Sheets

Figure 3B and C

EXPANDED NK CELLS

TECHNICAL FIELD

The present invention relates to expanded natural killer (NK) cells being cytotoxic against malignant cells and a method of treatment of malignant disease.

BACKGROUND ART

NK cells are cytotoxic lymphocytes that lyse certain tumor and virus infected cells without any prior stimulation or immunization. NK cells are also potent producers of various cytokines, e.g. IFN-y, TNF-α, GM-CSF and IL-3. Therefore, NK cells are also believed to function as regulatory cells in the immune system, influencing other cells and responses.

In humans, NK cells are broadly defined as CD56+CD3− lymphocytes. The cytotoxic activity of NK cells is tightly controlled by a balance between the activating and inhibitory signals from receptors on the cell surface. A main group of receptors that inhibits NK cell activation are the inhibitory killer immunoglobulin-like receptors (KIRs). Upon recognition of self MHC class I molecules on the target cells, these receptors deliver an inhibitory signal that stops the activating signalling cascade, keeping cells with normal MHC class I expression from NK cell lysis. Activating receptors include the natural cytotoxicity receptors (NCR) and NKG2D that push the balance towards cytolytic action through engagement with different ligands on the target cell surface. Thus, NK cell recognition of target cells is tightly regulated by processes involving the integration of signals delivered from multiple activating and inhibitory receptors.

Several strategies have been used to enhance NK cell responses to tumors. Cytokines are used in the treatment of some human cancers and NK cell differentiation and activation is affected by cytokines such as interleukins (e.g. IL-2, IL-12. IL-15, IL-18 and IL-21). The effect of IL-2 administration on activation and expansion of NK cells in cancer patients have been assessed in several trials with mixed outcomes depending on type of tumor and the conditions used for IL-2 administration. One example of cellular therapy is the NK cell-mediated killing of leukaemia cells which is based on NK cell alloreactivity.

Multiple myeloma (MM) is a plasma cell neoplasm characterized by the clonal proliferation of plasma cells in the bone marrow (BM). The malignant cells are associated with the synthesis of monoclonal immunoglobulin and a high incidence of osteolytic bone lesions. The disease accounts for about 2% of all cancer deaths and nearly 20% of deaths caused by hematological malignancies. Although allogeneic stem cell transplantation occasionally cures these patients and drugs like thalidomide, lenalidomide and bortezomib have improved outcome, high-dose chemotherapy followed by autologous stem cell transplantation (ASCT) still appears to be the best treatment for patients up to 65-70 years of age. However the great majority of patients with MM are incurable due to the persistence of minimal residual disease. Thus, novel methods for complementing or improving current treatments are needed.

In order to use NK cells in adoptive immunotherapeutic strategies, the availability of functionally active NK cells on a clinical scale is crucial. Clinical trials that have been performed using autologous NK cells were hampered by the fact that the cell dose was inadaptable to the demands of clinical trials. Therefore, the development of protocols for large-scale generation of NK cells is important to evaluate the potential of NK cell-based therapeutic protocols. Examples of reports that deal with ways of expanding and culturing human NK-cells are U.S. Ser. No. 10/242,788 and WO 2006/052534.

Human ex vivo expanded NK cells would be favorable candidates for immunotherapeutic approaches against malignant disease if they could target tumor cells.

Aims of the Invention

One aim of the invention is to provide expanded and active CD56+CD3− NK cells.

Another aim of the invention is to provide expanded CD56+CD3− NK cells that are cytotoxic against cells of malignant disease.

Yet another aim is to provide a method of treatment of a malignant disease.

SUMMARY OF THE INVENTION

The present invention relates to ex vivo expanded natural killer (NK cells) that can be used for immunotherapy of tumor cells, the NK cells showing no significant cytotoxicity against normal cells. The NK cells according to the invention are ex vivo expanded and active cells having the phenotype CD56+CD3−. This phenotype is specifically toxic against tumor cells. Upregulation of at least one activating receptor contributes to the cytotoxic activity of the expanded NK cells. In one embodiment the invention relates to a composition comprising the NK cells according to the invention.

In another embodiment the present invention relates to a method of treatment of a malignant disease wherein NK cells according to the invention or a composition according to the invention are/is administered to a patient with a malignant disease, or a patient undergoing autologous stem cell transplantation for cancer, or a patient with a malignant disease following allogeneic stem cell transplantation, or a patient with haematological malignancies, or a patient with solid tumors, in a pharmaceutically effective dose.

DISCLOSURE OF THE INVENTION

Before the present invention is described, it is to be understood that the terminology employed herein is used for the purpose of describing particular embodiments only and is not intended to be limiting, since the scope of the present invention will be limited only by the appended claims and equivalents thereof.

It must be noted that, as used in this specification and the appended claims, the singular forms "a," "an," and "the" include plural referents unless the context clearly dictates otherwise.

Also, the term "about" is used to indicate a deviation of +/−2% of the given value, preferably +/−5%, and most preferably +/−1O % of the numeric values, where applicable.

Given their strong cytolytic activity and the potential for auto-reactivity, natural killer (NK) cell activity is tightly regulated. In order to kill cells with a missing or abnormal MHC class I expression the NK cells need to be activated. NK cells must receive an activating signal which can come in a variety of forms, the most important of which are cytokines, Fc receptors, activating and inhibitory receptors. In the content of the present invention the term "activated NK cells" refers to NK cells that have received an activating signal, thus being capable of killing cells with deficiencies in MHC class I expression.

In the content of the present invention the term "NK cell expansion" relates to the culturing of NK cells that go through a series of cell division and thus expand in number of cells present in the culture. The term "expanded NK cells" relates to NK cells obtained through NK cell expansion. More specifically, in one embodiment the term "expanded NK cells" relates to a polyclonal group of chronically activated CD56+CD3− cells, expanded in a specific cGMP grade environment and cGMP grade medium.

In the content of the present invention the term "upregulation of receptor" relates to the increase in receptor density per cell.

In the content of the present invention cells that have a "cytotoxic phenotype" relates to cells that are toxic, i.e. they induce the death of other cells such as, but not limited to, tumor cells, infected cells or cells that are otherwise damaged or dysfunctional. Cytotoxic cells of the present invention are mainly toxic to tumor cells. The cytotoxicity of NK cells towards other cells can easily be measured, for example, by traditional cell counting before and after exposure to the NK cells according to the invention. Such methods are well known to a person skilled in the art. Examples of suitable methods are, but not limited to, fluorescent cell counting assay, immunofluorescent cell counting assay, cell viability assay, and flow cytometry-based cytotoxicity assay.

In the context of the present invention the term "effector cell" relates to a cell that performs a specific function in response to a stimulus such as cells in the immune system. In one embodiment effector cells are a type of lymphocytes that are actively engaged in secreting antibodies. Non-limiting examples of effector cells are NK cells, T cells and NK-like T cells Ex vivo expansion and reinfusion of natural killer (NK) cells to patients afflicted with a malignant disease offers a new potentially interesting therapeutic approach to combat such a disease. A prerequisite for this is the possibility to expand and use NK cells that meet the demands of clinical trials. The present inventors have surprisingly shown that ex vivo expanded NK cells can be used for immunotherapy of tumor cells that often express varying levels of MHC class I molecules, the NK cells showing no significant cytotoxicity against normal cells.

Accordingly, the present invention relates to ex vivo expanded and activated natural killer cells having the phenotype CD56+CD3−. The NK cells according to the invention are expanded, active and have a phenotype cytotoxic against tumor cells, preferably autologous tumor cells. The NK cells can be obtained from any conventional source and are preferably derived from peripheral blood, bone marrow, cord blood, cell lines or cytokine stimulated peripheral blood. NK cells can, for example; be expanded from a sample of peripheral blood mononuclear cells (PBMCs). PBMCs are a mixture of monocytes and lymphocytes; blood leucocytes from which granulocytes have been separated and removed. The culture conditions are outlined below in "Experimentals". According to the present invention the NK cells should be expanded for at least about 5 days, preferably not less than about 10 days, more preferably not less than about 15 days and most preferably not less than about 20 days. Already after 5 days the NK cells can show anti-tumor activity.

Furthermore, in one embodiment of the invention the NK cells according to the invention should be expanded at least about 100 fold, preferably at least about 200 fold, more preferably at least about 400 fold, more preferably at least about 600 fold, more preferably at least about 1000 fold and even more preferably at least about 1500 fold.

The activating pathway of NK cells also includes a series of different receptors. Activating receptors do not directly signal through their cytoplasmic tail, but instead associate non-covalently with other molecules containing ITAMs (immunoreceptor tyrosine-based activation motifs), that serve as the signal transducing proteins. Thus, according to one embodiment of the invention the ex vivo expanded and activated NK cells have an upregulated expression of at least one activating receptor. Non-limiting examples of activating receptors are: CD16 (FcγRIII), CD25 (IL-2Rα), CD27, CD28, CD69, CD94, CD122 (IL-2Rβ), CD161, CD226 (DNAM-1), 2B4 (CD244), CD314 (NKG2D), KIR2S, KIR3S, NCRs (natural cytotoxicity receptors) such as NKp30, NKp44, and NKp46, CD85H (ILT-1) and IFN-α/βB. Preferably said at least one activating receptor is selected from the group consisting of 2B4, CD8, CD16, CD 27, CD226, NKG2D, NKp30, NKp44 and NKp46. In one embodiment of the present invention the at least one activating receptor is 2B4 or CD226.

The NK cells according to the present invention exhibit higher degranulation activity compared to non-expanded NK cells. The degranulation activity can be estimated through the determination of the CD107a expression. CD107a surface expression correlates closely with degranulation and release of cytotoxic granules. Degranulation as measured by CD107a expression correlates to cytotoxic activity of an effector cell, such as an NK cell. The method of determining degranulation activity through the determination of CD107a expression is well known to a person skilled in the art. See, for example, Alter G, Malenfant J M, Altfeld M. CD107a as a functional marker for the identification of natural killer cell activity. J Immunol Methods. 2004; 294: 15-22.

The change in receptor expression can be calculated by mean fluorescence intensity (MFI) ratios:

$$MFI_{dayX}/MFI_{day0}$$

where x is the number of days of expansion of the NK cell.

When the MFI for day X samples is higher than for day 0, the MFI ratio will be higher than 1, which indicates the relative extent of upregulation in that receptor. Thus, a MFI ratio of e.g. 1.5 would mean a 50% of upregulation of a specific receptor. The calculation of MFI ratios is well known to persons skilled in the art.

According to one embodiment of the present invention the at least one activating receptor is upregulated by at least about 50%, preferably at least about 75, more preferably at least about 100% and most preferably at least about 200%.

According to another embodiment of the invention the NK cells have a downregulated expression of at least one receptor, such as an inhibitory receptor or a chemokine receptor (e.g. CCR7). Non-limiting examples of inhibiting receptors are inhibitory killer immunoglobulin-like receptors (KIRs). Further non-limiting examples of inhibiting receptors are GL183, KIR2DL1, Lir-1, NKB1, and NKG2A. It is possible that none inhibitory receptor can be downregulated in some patients, one inhibitory receptor downregulated in some patients and more than one in some patients. Thus, in one embodiment of the invention the NK cells according to the invention can have an upregulated expression of at least one activating receptor and a downregulated expression of at lest one receptor. In another embodiment the NK cells according to the invention can have an upregulated expression of at least one activating receptor and a down-regulated expression of at lest one inhibitory receptor.

According to another embodiment of the present invention the expanded and activated NK cells have at least about 100% increased cytotoxicity compared to non-ex vivo expanded NK cells. Preferably at least about 150%, more preferably at least about 200% and most preferably at least about 400% increased cytotoxicity compared to non-expanded NK cells. Non expanded NK cells relates to freshly isolated NK cells and short-term activated NK cells. In the context of this invention the expression "short term activated" means NK cells that have been expanded over night only.

The increased cytotoxicity of the expanded and activated NK cells can also be an effect mediated by an upregulation of a combination of receptors. Thus, in yet another embodiment the present invention relates to expanded and activated NK cells having an upregulated expression of more than one receptor. Thus, recognition of the target cell by NK cells can involve a combination of receptors that synergistically deliver activating signals.

Another embodiment of the present invention relates to a composition comprising the expanded and active NK cells as described above. In addition to the NK cells, a composition according to the invention may also contain any suitable physiological buffer, such as, but not limited to, phosphate buffered saline. Suitable physiological buffers are well known to the skilled person. Other substances, such as, but not limited to cytokines such as IL-2 and its derivatives, immunomodulatory drugs and proteosome inhibitors, that increase the effect of the administered cells can also be added to the composition or administered separately. In one embodiment the composition also contains lower levels of other cells. Non-expanded PBMCs usually contain a mixture of different cells, for example, NK cells (CD56+CD3−) NK-like T cells (CD56+CD3+) and T cells (CD56-CD3+). After expansion NK cells are the dominating cell type in the culture but also other cell types can be present in the expanded culture.

The NK cells according to the invention can also be administered or used in combination with other cancer therapies, such as, but not limited to, surgery, radiation and cytotoxic drugs.

Several experimental studies have shown that NK cells can eliminate cancer cells. The results of the study underlying the present invention suggest that ex vivo expanded and activated cells have a promising anti-tumor potential compared to resting NK cells. Thus, the present invention also relates to NK cells being cytotoxic against tumor cells, said tumor cells preferably being autologous tumor cells. Autologous tumor cells refer to cells that are reimplated in the same individual as they came from, i.e. the donor and the recipient are the same person. Allogeneic tumor cells, on the other hand, refers to cells taken from different individuals of the same species, i.e. genetically non-identical individuals. Two or more individuals are said to be allogeneic to one another when the genes at one or more loci are not identical.

The NK cells according to the present invention are cytotoxic against tumor cells, said tumor cells being selected from, but not limited to, the group consisting of haematological tumors or malignancies and solid tumors or malignancies. Haematological tumors or malignancies include types of cancer that affects the blood, the bone marrow and the lymph nodes. In particular the NK cell according to the invention is cytotoxic against cells of lymphoma (e.g. Hodgkin's disease and non-Hodgkin's lymphoma), multiple myeloma (MM), and leukaemia (e.g. acute lymphoblastic leukemia, acute myelogeneous leukaemia, chronic myelogeneous leukaemia, chronic lymphocytic leukaemia, hairy cell leukaemia). Examples of solid tumors are, but not limited to, hepatocellular tumors, gastrointestinal tumors (such as colon tumors), ovarian tumors, renal tumors, lung tumors and pancreatic tumors. In one particular embodiment of the present invention the NK cells are cytotoxic against multiple myeloma cells.

Since large numbers of activated NK cells now can be produced and used in the setting of adoptive immunotherapy, the present invention also relates to a method of treatment. In leukemia patients autologous ex vivo expanded and activated NK cells might be helpful for treatment of minimal residual disease (MRD) after autologous stem cell transplantation. According to the invention it would be advantageous to administer autologous ex vivo cultured NK cells, either prophylactically or therapeutically, to patients undergoing autologous hematopoietic stem cell transplantation for diseases such as multiple myeloma which have in general a poor prognosis with high incidence of progressive disease post transplant. Ex vivo expanded NK cells of donor origin can be used for the treatment of recurrent malignant disease following allogeneic stem cell transplantation. Autologous NK cells can be administered, either prophylactically or therapeutically, to patients undergoing autologous stem cell transplantation for cancer. Other ways of using autologous NK cells is for ex vivo purging of malignant cells in the harvest, for treatment of patients with hematological malignancies, and as a cellular therapy for solid tumors.

Another embodiment of the invention is therefore a method of curative or prophylactic treatment, wherein expanded, activated and cytotoxic NK cells with the phenotype CD56+CD3−, as described above, are administered to patients with a malignant disease, or to a patient with a malignant disease following allogeneic stem cell transplantation, or patients undergoing autologous stem cell transplantation for cancer, or patients with hematological malignancies, or patients with solid tumors, in a pharmaceutically effective dose. A patient can also be treated with the inventive method in order to prevent recurrence of a malignant disease.

In another embodiment of the inventive method a composition comprising the NK cells is administered to patients with a malignant disease or patients undergoing autologous stem cell transplantation for cancer, or to a patient with a malignant disease following allogeneic stem cell transplantation or patients with hematological malignancies, or patients with solid tumors, in a pharmaceutically effective dose. The composition according to the invention can also be administered to a patient in order to prevent recurrence of a malignant disease.

Examples of malignancies/tumors that can be treated with the inventive method are outlined above.

In the inventive method a sample (e.g from peripheral blood, bone marrow, or cord) is taken from a patent afflicted with a malignant disease. In one embodiment the patient has been treated with conventional cancer therapies but the treatment has been unsuccessful or the malignancy has recurred. The method can also be a prophylactic treatment, for example, to prevent recurrence of a malignant disease. Before culturing the cells (e.g. PBMCs), they are purified and separated according to methods well known for the skilled person. The cells are thereafter ex vivo expanded as outlined above and in the "Examples". Subsequently, the expanded cells are administered to the patient. The patient is thereafter carefully followed-up in order to determine if the patient has responded well to the treatment and to determine if the treatment is to be repeated. Samples can, for example, be taken from blood, bone marrow and or urine for follow-up of the treatment at regular time intervals.

In the inventive method the NK cells are preferably are ex vivo expanded for at least about 5 days, preferably not less than about 10 days, more preferably not less than about 15 days and most preferably not less than about 20 days before administration to the patient.

In another embodiment the NK cells have been expanded at least about 100 fold, preferably at least about 200 fold, and more preferably at least about 400 fold, preferably at least about 600 fold, more preferably at least about 1000 fold and even more preferably at least about 1500 fold compared to day 0 of expansion, before administration to a patient.

The inventive method can be performed once or repeated several times. In one embodiment the NK cells according to the invention are administered to the patient about 1-10 times, preferably about 1-7 times, more preferably about 1-5 times and most preferably about 1-3 times. The administration route can be any suitable way of administration well known to the skilled person for example, but not limited to; intravenous, intraperitoneal and intratumoral administration. The dosage can be the same in all administrations or for example high in the first administration(s) and than lower in subsequent administrations.

Administration, alone or in combination with the NK cells of the invention, of subcutaneous IL-2 or its derivatives as well as immunomodulatory drugs such as, but not limited to, thalidomide or proteosome inhibitors such as, but not limited to, bortezomib, may further increase the effect of administered cells.

The features of the ex vivo expanded and activated NK cells to be used in the method of treatment are as described above for the NK cells according to the invention.

BRIEF DESCRIPTION OF THE FIGURES

The invention is further described in the description, examples and claims with reference to the attached figures in which:

MODE(S) FOR CARRYING OUT THE INVENTION

The invention will now be further described in the experiments outlined below wherein efficient ex vivo NK cell expansion from PBMCs (peripheral blood mononuclear cells) of Multiple Myeloma (MM)+ patients using clinical grade components is demonstrated. Furthermore, the ability of these NK cells to kill autologous tumor cells is shown. These data suggest the possibility of using autologous ex vivo expanded NK cells for immunotherapy of MM.

EXPERIMENTAL

Patients and Acquisition of Patient Material

Peripheral blood and bone marrow (BM) samples from seven newly diagnosed patients at different stages of MM were included in the study. The patients were followed at the Department of Hematology, Karolinska University Hospital Huddinge, Stockholm, Sweden. The study was approved by the local research ethics committee. Informed consents were obtained from all patients. Patients' characteristics at the time of blood and BM sampling for the study are given in Table 1.

TABLE 1

Patient characteristics at the time of blood and bone marrow sampling for the study.

| Patient* | Age | Gender | MM Stage (Durie&Salmon) | MM Type |
|---|---|---|---|---|
| 1 | 41 | Male | IIIB | IgG-/. . . IgG-λ |
| 2 | 80 | Male | IB | IgG-/. . . IgG-λ |
| 3 | 80 | Male | IIIB | Light chain-λ |
| 4 | 75 | Female | IIA | IgG-/. . . IgG-λ |
| 5 | 66 | Female | IIB | IgG-/. . . IgG-λ |
| 6 | 53 | Female | IA | IgG-K IgG-λ |
| 7 | 64 | Male | IIB | Light chain-κ |

+All the patients included in this study were diagnosed in the first half of 2006 and had not yet started any treatment regimen at sampling time.

PBMCs as well as BM mononuclear cells (BMMCs) were isolated by gradient centrifugation, using Lymphoprep (Axis-Shield, Oslo, Norway). PBMCs and BMMCs were washed twice with phosphate-buffered saline (PBS) (Gibco, Grand Island, N.Y., USA), and cell viability was assessed by Trypan blue exclusion. To avoid inter-experimental variability, PBMCs and BMMCs were directly frozen in human serum albumin (Baxter) containing 6% DMSO (Wak-chemie medical, Germany) for subsequent phenotyping and cytotoxicity experiments.

Example 1

Ex Vivo Expansion of NK Cells from PBMCs

Material & Methods:

The culture conditions for the expansion of cytotoxic cells have previously been optimized on PBMCs from healthy individuals (Carlens et al., Hum. Immunol. 2001; 62:1092-1098). Briefly, PBMCs were initially thawed and cultured in T25 flasks (TPP, Trasadingen, Switzerland) at a concentration of $0.5 \times 10^6$ cells/ml in CELLGRO SCGM serum-free medium (CellGenix, Freiburg, Germany) with the addition of 5% human serum (Biowhittaker-Cambrex, MD, USA) and 500 Um/ml rhIL-2 (Proleukin®, Chiron Corporation, Emeryville, Calif., USA). For the first 5 days, the medium was further supplemented with anti-CD3 antibody (Orthoclone OKT-3, Ortho Biotech Inc., Raritan, N.J., USA) to a final concentration of 10 ng/ml. On day 5 of culture, the OKT-3-containing medium was washed out, and fresh medium with IL-2 (500 U/ml) and 5% human serum was added. The cultures were then replenished with fresh medium every other day throughout the culture period. Total cell numbers were assessed by staining cells with Trypan blue dye on days 0, 5-6, 9-10, 14-15, and 20 of culture. Absolute cell counts were calculated by multiplying the total number of cells with the percentage of these subsets determined by flow cytometry. To prevent contact inhibition of cell growth, the cells were transferred to bigger flasks when necessary. The final products were evaluated for purity, viability and phenotype.

Figure 1:
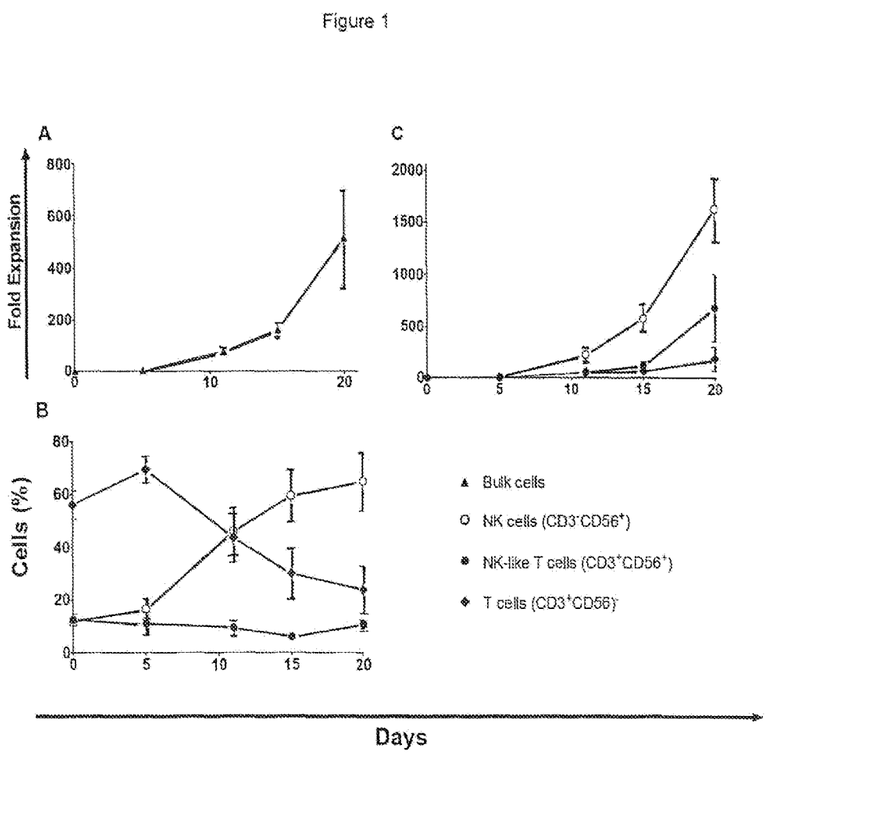
FIG. 1 shows expansion dynamics of blood and bone marrow samples obtained from seven multiple myeloma patients and cultured for 20 days under identical conditions. Bulk cells in culture expanded to a total of 511 fold (A). Initial OKT-3 treatment lead to an increased percentage of T cells in the culture during the first five days of culture followed by a decrease after withdrawal of OKT-3 (B). The subsequent increase continued until finally NK cells dominated in the culture (C). Results are shown as means+SD.

Results:

In order to study whether it is possible to expand NK cells from MM patients using GMP grade components, cultures of PBMCs from seven patients with MM were established. At the start of the culture (day 0), the mean percentage of NK cells (CD56+CD3−) was 11% (range: 7-17%) whereas T cells constituted 57% (range: 36-81%). NK cell expansion approached log-linearity after an initial non-proliferative phase of about five days. By day 20, the total cell population had expanded on average 511-fold (range: 123-1545) (FIG. 1A) and, of these, NK cells had expanded on average 1625-fold (range: 502-2658) (FIG. 1B). Due to the relatively greater expansion of NK cells compared to the other cell types, NK cells dominated the culture towards the end of the culture period, reaching on average 66% of the cells by day 20 (FIG. 1C). The percentage of NK-like T cells (CD56+CD3+) did not change significantly during the culture period (day 0: 14%, day 20: 18%), while the percentage of T cells (CD56−CD3+) declined following withdrawal of OKT3 at day 5, decreasing to an average of 14%. These results show that NK cells from MM patients can be expanded efficiently ex vivo by using the present 20 day culture approach.

Example 2

Flow Cytometry Based Phenotyping of NK Cells and NK Ligands on Multiple Myeloma (MM) Cells Material & Methods:

The cell phenotype and expansion dynamics of subpopulations were analyzed by flow cytometry on days 0, 5-6, 9-10, 14-15 and 20 of culture using standard procedures with flourochrome conjugated mAbs against the following surface antigens CD3, CD14, CD38, CD56 and CD138.

Day 0 and day 20 cells from all patients were subjected to a more detailed immunophenotypic analysis. To avoid inter-acquisition variability, all frozen samples were simultaneously thawed for a detailed phenotypic characterization of CD56+CD3− (NK) cell subset by flow cytometry. This panel included fluorochrome conjugated mAbs against the following surface antigens: CD2 (RPA-2.10), CD3 (UCHT-1), CD4 (SK3), CD7 (M-T701), CD8 (HIT8a), CD14 (MOP9), CD16 (3G8), CD19 (HIB19), CD25 (M-A251), CD27 (M-T271), CD38 (HIT2), CD56 (B159), CD57 (NK-1), CD161 (DX12), CD183 (3D12), CD184 (12G5), CD195 (207/CCR5), CD197 (1C6/CXCR3), CD226 (DX11), NKB1 (DX9), LFA-1 (HI111), CD62L (DREG56), CD69 (FN50) and CD138 (M115) purchased from BD Biosciences, San Jose, Calif., USA; CD48 (MEM102) from Biosource AB, Stockholm, Sweden; CD158B1/B2,j (GL183), CD244 (2B4) (C1.7), NKG2D (ON71), NKp30 (Z25), NKp44 (Z231), NKp46 (BAB281), LIR-1 (HP-F1), Valpha24 (C15), Vbetall (C21) from Beckman Coulter Inc., Fullerton Calif., USA; NKG2A (131411), NKG2C (134591), KIR2DL1 (143211), KIR2DL3 (180701) from R&D Systems, Minneapolis, Minn., USA All antibody stainings for flow cytometry were done according to the following protocol. Fc receptors were blocked by incubation with 1 μg human IgG per 105 cells for 15 minutes on ice. The cells were then washed once with PBS and incubated with appropriate amounts of antibody at 4° C. for 30 minutes followed by another wash with PBS. For both panels, LIVE/DEAD Fixable Red Dead Cell Stain (Invitrogen, Carlsbad, Calif., USA) was used for dead cell exclusion according to the manufacturer's instructions. Briefly, 1 μl of dye was applied to 1×106 cells resuspended in 1 ml of PBS and incubated on ice for 30 minutes. The labeled cells were then washed with PBS and fixed in 4% PFA prior to data acquisition. Cells were analyzed by nine-color flow cytometry (CyAn™ ADP LX, Dako A/S, Glostrup, Denmark) calibrated with CompBeads™ and appropriate isotype controls (BD Biosciences). The acquired data were analyzed with Dako Cytomation Summit software versions 4.2 and 4.3 (Dako A/S) and FlowJo software version 7.2 for PC (Tree Star Inc., Ashland, Oreg., USA) setting appropriate SSC/FSC gates around the lymphocyte population and using LIVE/DEAD Fixable Red Dead Cell Stain negative cells. From the lymphocyte gate, NK cells were gated as the CD56+CD3− population. NK-like T cells and T cells were gated as CD3+CD56+ and CD3+CD56− populations respectively. MM cells were gated as CD38+ CD138+. In each sample a minimum of 105 cells was analyzed.

For each cell surface receptor analyzed, mean fluorescence intensity (MFI) values were calculated for day 0 and day 20 samples. To estimate the change in receptor expression, MFI ratios were calculated (MFIday20/MFIday0) for each receptor. When the MFI for day 20 samples was higher than for day 0, the MFI ratio was higher than 1, which indicated the relative extent of up regulation in that receptor. Likewise, an MFI ratio below 1 was interpreted as down regulation in the expression of that receptor.

Figure 2A:
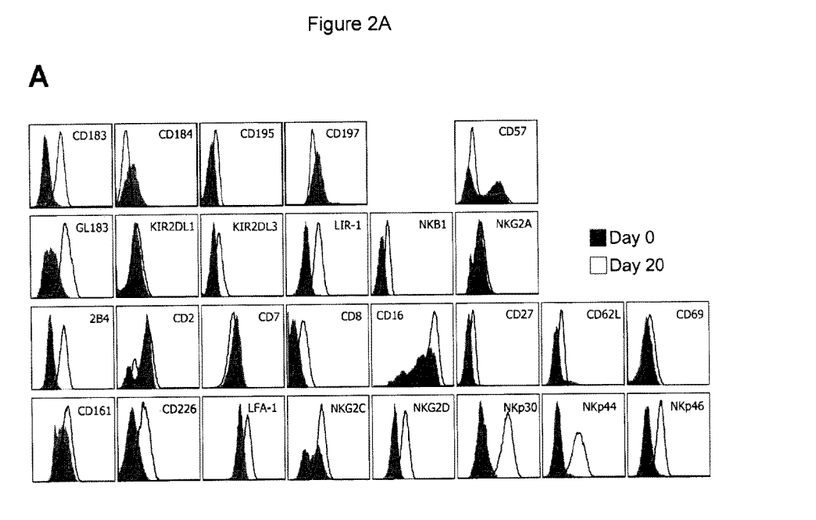
FIGS. 2A-B show changes in the receptor expression patterns of NK cells following expansion and activation. Representative data (Patient 5) showing comparative phenotyping of day 0 (grey) and day 20 (white) cells (FIG. 2A). Each patient's MFI ratios (•) of day 20 to day 0 as well as the medians (-) of seven patients were plotted for each receptor (FIG. 2B). The dashed line shows MFI ratios=1 which indicates unaltered receptor expression during the expansion period. Values above the line (MFI ratio>1) indicate upregulation and below (MFI ratio<1) denote downregulation.
Figure 2B:
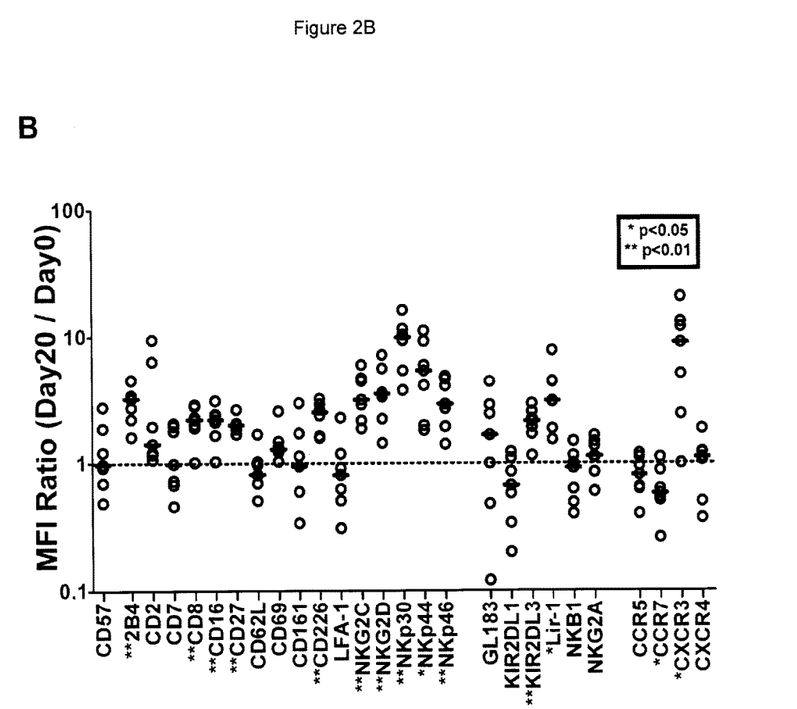

Results:

To characterize the final expansion product with respect to the starting material, a detailed flow cytometric analysis was undertaken (representative data of one patient is shown in FIG. 2A). For each receptor analyzed, MFI values were calculated in samples from day 0 and day 20 cultures and used their ratio (MFIday20/MFIday0) as an indicator of the change. FIG. 2B illustrates the MFI ratios of all patients for all receptors analyzed as well as the median values. Briefly, in the final product, the inventors observed a significantly upregulated expression of the following activating receptors: 2B4, CD8, CD16, CD27, CD226, NKG2C, NKG2D, NKp30, NKp44 and NKp46. The inhibitory receptors KIR2DL3 and LIR-1 were also upregulated. The chemokine receptor CCR7 was significantly downregulated whereas CXCR3 was markedly upregulated. No significant changes in the expression levels of CD2, CD7, CD57, CD62L, CD69, CD161, LFA-1, GL183, KIR2DL1, NKB1, NKG2A, CCR5 or CXCR4 were observed.

Example 3

Evaluation of Cell-Mediated Cytotoxicity

Material & Methods:

The cytotoxic capacity of NK cells before and after expansion was evaluated in vitro with a standard 4 hour 51Cr-release assay against NK-sensitive K562 cells. Because the 51Cr-release assay is not suitable for primary MM cells 16-18, a flow cytometry based cell mediated cytotoxicity assay was used.

For the 51Cr-release assay, K562 target cells were labelled with 100 µCi of 51Cr for one hour at 37° C., washed twice with PBS, and resuspended in 1 ml of RPMI medium. A total of $3 \times 10^4$ target cells in 100 µl RPMI medium was placed in triplicates into V-bottom 96-well plates and incubated for 4 hours with 100 µl of effector cells at appropriate concentrations to obtain effector:target ratios from 1:3 to 10:1. Aliquots of supernatants were then counted using a Packard Cobra Auto-Gamma 5000 Series Counting System (Meriden, Conn., USA). The percentage of specific 51Cr release was calculated according to the formula: percent specific release=[(experimental release−spontaneous release)/(maximum release−spontaneous release)]×100.

For the flow cytometry based assay, autologous MM cells or K562 controls were labelled with TFL4 reagent of the CytoToxilux-PLUS kit (OncoImmunin Inc., Gaithersburg, Md., USA) according to the manufacturer's instructions. $5 \times 10^4$ target cells were placed in tubes together with different amounts of effector cells to obtain effector:target ratios from 1:3 to 10:1 in a final volume of 300 µl RPMI medium and incubated at 37° C. for 4 hours. The cells were then washed once with PBS. Following Fc receptor blockade with IgG (1 µg/$10^5$ cells) on ice for 20 minutes to avoid antibody-dependent cellular cytotoxicity, the cells were incubated with appropriate amounts of fluorochrome conjugated mAbs against CD3, CD34, CD38, CD56 and CD138 at 4° C. for 30 minutes. After washing with PBS, the cells were resuspended in 500 µl of PBS containing 5 µg 7-aminoactinomycin D (7-AD; Invitrogen, Carlsbad, Calif., USA) and incubated in the dark for an additional 15 minutes at 4° C. before data acquisition by nine-color flow cytometry. Cytotoxicity was assessed according to the following formula: percent killing=[(experimental death-spontaneous death)/(maximum death-spontaneous death)]×100.

To compare cytotoxicity of short term activated and expanded cells, day 5 cells from three patients were also tested for cytotoxicity against K-562 cell line and primary autologous myeloma cells.

For blocking experiments, effector cells were preincubated at 4° C. for 30 minutes with 10 µg/ml of isotype controls or the mAbs against the following receptors: 2B4 (C1.7)19, CD226 (DX11)20, NKG2C (134522), NKG2D (1D11)21, NKp30 (Z25)22, NKp44 (Z231)22, NKp46 (BAB281)22, and CD27 (1A4)23.

Figure 3A:
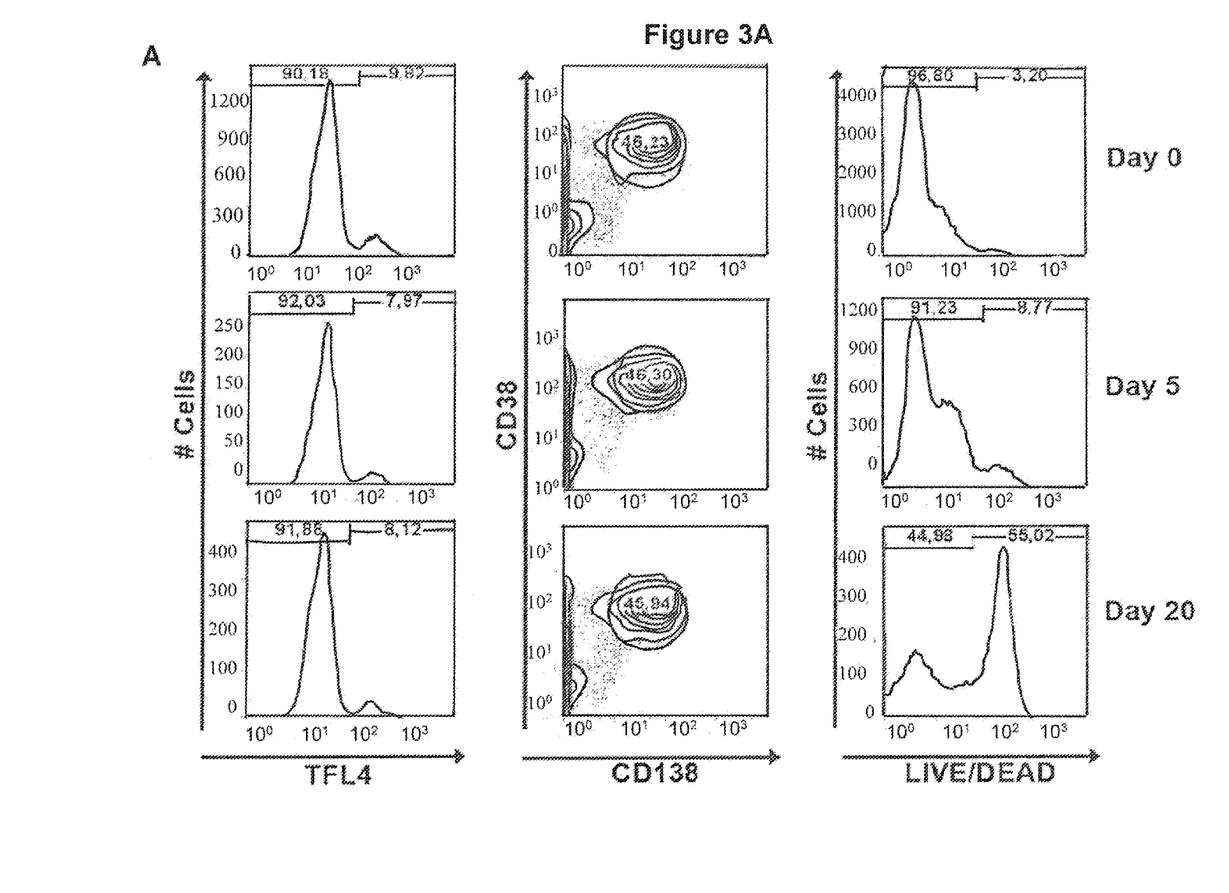
FIGS. 3A-C show the results from the cell mediated cytotoxicity assays. NK cell cytotoxicity against K562 cell line was measured by the standard chromium release assay and flow cytometry based cytotoxicity assay (FIG. 3A). The flow cytometry based cytotoxicity assay demonstrates an increased cytotoxicity of expanded NK cells (day 20) against autologous MM cells compared to freshly isolated NK cells (FIG. 3B). Expansion and activation of the cells did not affect the cytotoxicity against autologous normal BM cells (FIG. 3B). Representative data (Patient 5) is shown to demonstrate the analysis procedure (FIG. 3C).

Results:

The inventors next investigated the cytotoxic activity of ex vivo expanded NK cells against a standard NK target cell line, K562. Cytotoxicity against K562, measured by a flow cytometry-based cytotoxicity assay and confirmed by a standard 4-hour chromium release assay, was markedly increased by day 20 NK cells when compared to day 0 and day 5 cells (FIG. 3A). At a 10:1 effector to target cell ratio, 62% of the K562 targets were killed by the day 20 NK cells whereas day 0 and day 5 cells killed only 8% and 29% of K562 targets, respectively, at a similar effector to target ratio.

Figure 3B:
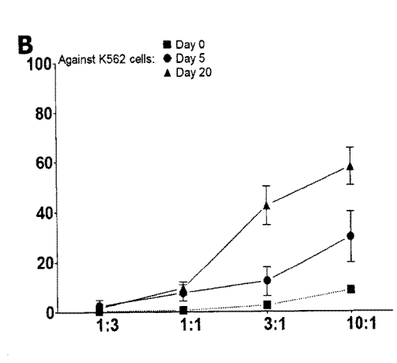
Figure 3C:
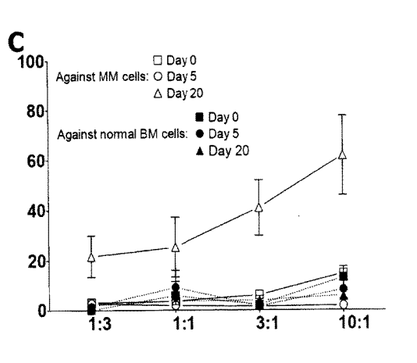

In an in vivo immunotherapy approach, the present NK cells would only be useful if they are able to target autologous MM cells. The inventors thus assessed cytotoxicity against autologous MM cells by a flow cytometry based assay. At day 20, marked cytotoxic activity of NK cells against autologous MM cells was observed whereas both day 0 and day 5 cells showed no or only low levels of cytotoxicity (FIG. 3B). At a 10:1 effector:target ratio, 61% of autologous MM cells were killed by day 20 cells (representative data of one patient is shown in FIG. 3c). Notably, no significant cytotoxicity against non-MM (CD138−) cells was observed. Ex vivo expanded NK cells show increased cytotoxicity against autologous MM cells.

Figure 4:
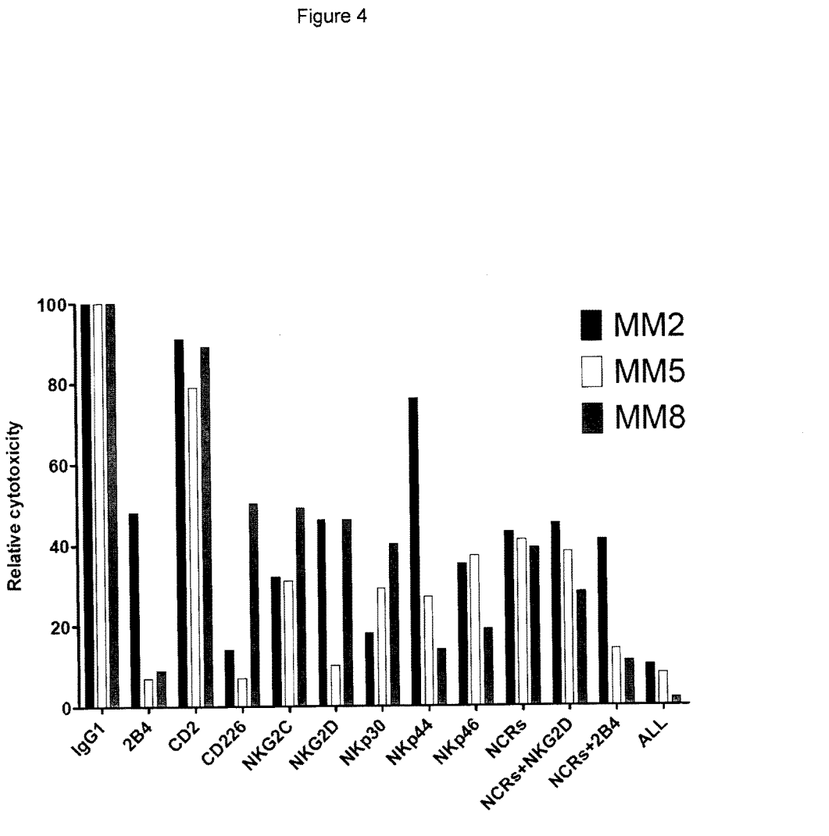
FIG. 4 shows blocking of activating receptors on NK cells. The results are shown as mean 522 inhibition+SD (N=3).

To determine the relative contributions of different activating receptors on autologous MM cytotoxicity, effector cells were preincubated with blocking antibodies against several individual activation receptors, or their combinations, and then co-incubated with autologous MM cells. Cytotoxicity was partially inhibited by blocking 2B4 (60% inhibition), CD226 (DNAM-1; 53%), NKG2C (48%), NKG2D (49%), CD27 (50%), NKp30 (57%), NKp44 (55%), and NKp46 (59%) (FIG. 4). This indicates that several activating receptors may contribute to MM cytotoxicity in line with current knowledge of receptor synergy for induction of cytotoxicity. Thus, the cytotoxicity against autologous MM involves target cell interaction with activating NK cell receptors.

Example 4

Analysis of NK Cell Degranulation

Material & Methods:

NK cells were coincubated with target cells at a ratio of 1:1 in a final volume of 200 µl in round-bottomed 96-well plates at 37° C. and 5% $CO_2$ for 6 h. Fluorochrome-conjugated anti-CD107a mAb or the corresponding IgG1 isotype control was added at the initiation of the assay. After 1 h of coincubation, Monensin (GolgiStop, Becton Dickinson) was added at a 1:100 dilution. Surface staining was done by incubating cells with anti-CD3 and anti-CD56 mAbs for 30 mins on ice. The cells were then washed, resuspended in PBS and immediately analyzed by flow cytometry.

Figure 5A:
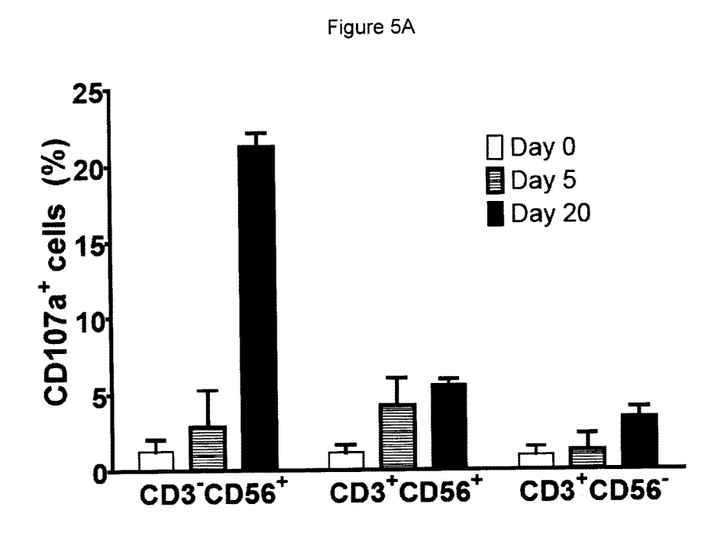
FIGS. 5A-B show CD1O7a mAb based degranulation assay against primary MM cells. Representative data (Patient 5) demonstrating the expression of CD107a on NK cells after contact with the NK sensitive K562 cell line and autologous MM cells (FIG. 5A). Comparison of CD1O7a expression on day 0, 5 and 20 NK cells upon contact with 519 autologous MM cells (FIG. 5B). The results are shown as percent CD1O7a cells+SD (N=3).
Figure 5B:
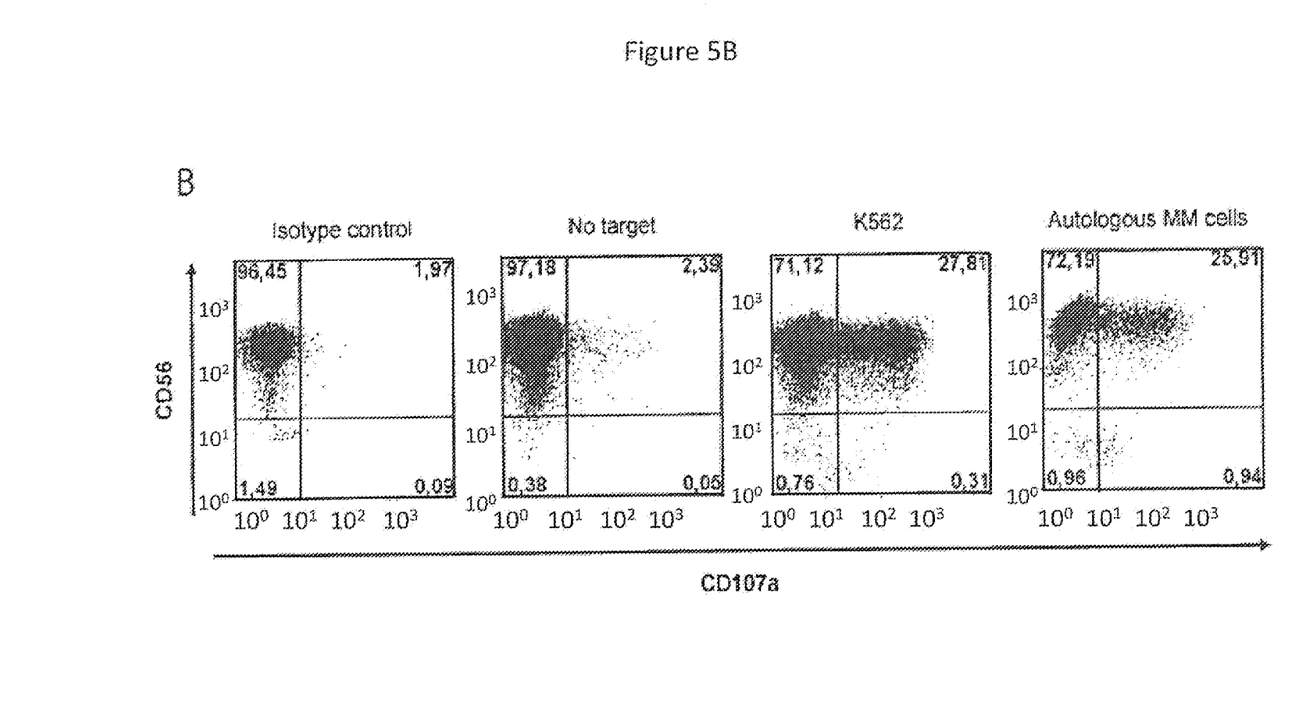

Results:

In order to better pinpoint the active population within the final expansion product showing cytotoxicity against autologous MM cells, the inventors shifted focus from MM cell lysis to effector cell activation by analyzing the surface expression of CD107a on different subpopulations upon contact with MM cells. CD107a expression correlates closely with degranulation and release of cytotoxic granules. Approximately 30% of Day 20 NK cells expressed CD107a on the cell surface on contact with K562 cell line. Similar degranulation was observed against autologous MM cells (representative data of one patient is shown in FIG. 5A). Analysis of expanded cells showed that NK cells were the main degranulating population following challenge with autologous MM cells (FIG. 5B). Thus, autologous MM cells trigger degranulation of ex vivo expanded NK cells.

Discussion

Example 1-4

Although previous reports suggest that cytokine activation of NK cells may lead to a better recognition of MM cells, MM cells are considered to be resistant to lysis by resting and short term activated autologous NK cells. Similar to the immune system defects mentioned above, this resistance has been explained by NK cell dysfunctions in MM patients including impaired NK cytotoxicity and increased levels of soluble IL-2 receptors as well as decreased expression of a number of activating receptors compared to healthy controls. The results indicate that expansion and/or long term activation of NK cells may reverse this potential dysfunction, since it was paralleled by induction of surface expression of CD107a and cytotoxicity of autologous MM. Based on assessment of induction of degranulation measured by expression of CD107a, it was concluded that expanded NK cells are the major effector compartment exerting autologous anti-MM activity under the present experimental conditions. Within the course of the present studies the inventors also phenotyped the expanded NK cells. This allowed a comparison of day 0 and day 20 NK cells. Since a balance of activating and inhibitory signals regulates NK cell function, optimal NK cell effector function is expected to occur in situations where the expression of activating NK cell receptors is adequate and not suppressed by inhibitory signals. Reduced 2B4 expression in NK cells from MM patients has been suggested to play a role in the immune escape mechanism of MM expressing its ligand CD4841, however it cannot be excluded that it might be a consequence of interactions between NK and MM cells. The upregulation of 284 after ex vivo expansion is likely one factor contributing to the cytotoxicity observed against autologous MM cells. Furthermore, NCRs and NKG2D, which presumably take part in the recognition of MM cells by NK cells, are significantly upregulated, suggesting possible pathways for autologous MM cell killing. The upregulation of CD226 which is a tumor surveillance receptor on NK cells, and a potent inducer of cytotoxicity against many tumor cell lines of hematopoetic and non-hematopoetic origin, could also contribute to the increase in cytotoxicity. Furthermore, it has previously been shown that CD27 NK cells are tightly regulated by inhibitory receptors whereas CD27 high NK cell subset is more cytotoxic. The upregulation of CD27 during expansion may also contribute to elevated levels of cytotoxicity.

Recently published results of clinical trials testing NK cell based immunotherapy involve infusion of resting and short-term IL-2 activated NK cells to patients with malignancies. These trials have shown that adoptively transferred NK cells are well tolerated. The present results shows that the present ex vivo expanded autologous NK cells have a promising anti-MM potential compared to resting or short-term activated NK cells. The high levels of NK cell expansion using cGMP quality components is of particular importance in relation to reaching an appropriate infusion dose in settings of immunotherapy.

A concern for the use of activated NK cells, especially in the allogeneic settings, is that they could cause a tissue damaging reaction. The present data shows that the recognition of autologous MM cells by ex vivo expanded NK cells involve a certain degree of specificity. The inventors demonstrated that day 20 NK cells lysed MM cells but spared non-MM cells from the same patient.

Although particular embodiments have been disclosed herein in detail, this has been done by way of example for purposes of illustration only, and is not intended to be limiting with respect to the scope of the appended claims that follow. In particular, it is contemplated by the inventor that various substitutions, alterations, and modifications may be made to the invention without departing from the spirit and scope of the invention as defined by the claims.

The invention claimed is:

1. A method of treating multiple myeloma by administering to a patient, a composition comprising natural killer (NK) cells produced by:
    (a) isolating NK cells from peripheral blood or bone marrow of a patient suffering from multiple myeloma, and
    (b) expanding the isolated NK cells ex vivo in the presence of autologous mononuclear cells for about 20 days, in a serum-free stem cell growth medium comprising human albumin, human recombinant insulin, L-glutamine and β-mercaptoethanol (CELLGRO SCGM), wherein said medium is supplemented with anti-CD3 antibody, human serum, and IL-2 for about the first 5 days, and wherein said medium is supplemented with IL-2 and human serum for the remainder of the about 20 days, whereby the expanded said NK cells have:
        (i) at least about a 100% increased cytotoxicity against multiple myeloma cells of said patient compared to freshly isolated non-expanded NK cells isolated from said patient, and
        (ii) an upregulated expression of at least one natural cytotoxic receptor (NCR).

2. The method according to claim 1, wherein said natural cytotoxic receptor is upregulated by at least about 50% compared to freshly isolated non-expanded NK cells isolated from said patient.

3. The method according to claim 1, wherein said at least one natural cytotoxic receptor is selected from the group consisting of 2B4, CD8, CD16, CD27, CD226, NKG2D, NKp30, NKp44 and NKp46.

4. The method according to claim 1, wherein said NK cells exhibit higher degranulation activity compared to freshly isolated non-expanded NK cells isolated from said patient as determined by CD107a expression.

5. The method according to claim 3, wherein said at least one natural cytotoxic receptor is 2B4.

6. The method according to claim 5, wherein said NK cells further have an upregulated expression of a second natural cytotoxic receptor compared to freshly isolated non-expanded NK cells isolated from said patient, wherein the second activating receptor is selected from the group consisting of CD8, CD16, CD27, CD226, NKG2D, NKp30, NKp44 and NKp46.

* * * * *